(12) United States Patent
Allen et al.

(10) Patent No.: US 7,807,199 B2
(45) Date of Patent: Oct. 5, 2010

(54) ANTIMICROBIAL COMPOSITION

(76) Inventors: Thomas K. Allen, 1704 Mulligan Pl., Manhattan, KS (US) 66502; Otto Carl Wilson, 301 Farm Rd., Aberdeen, MD (US) 21001

( * ) Notice: Subject to any disclaimer, the term of this patent is extended or adjusted under 35 U.S.C. 154(b) by 0 days.

(21) Appl. No.: 11/513,978

(22) Filed: Aug. 30, 2006

(65) Prior Publication Data

US 2008/0057135 A1    Mar. 6, 2008

(51) Int. Cl.
*A61K 9/14* (2006.01)
*A61K 33/38* (2006.01)
*A01N 59/16* (2006.01)

(52) U.S. Cl. .................... 424/489; 424/618

(58) Field of Classification Search ........... 424/400, 424/489, 618, 630, 649
See application file for complete search history.

(56) References Cited

U.S. PATENT DOCUMENTS

| | | | |
|---|---|---|---|
| 6,616,922 B2 * | 9/2003 | Taylor et al. ............ | 424/70.28 |
| 7,147,873 B2 * | 12/2006 | Scholz et al. ............ | 424/672 |
| 2004/0142046 A1 * | 7/2004 | Quillin .................... | 424/718 |
| 2005/0256026 A1 * | 11/2005 | Hodge et al. ............ | 510/504 |
| 2006/0182813 A1 * | 8/2006 | Holladay ................. | 424/618 |
| 2007/0003603 A1 * | 1/2007 | Karandikar et al. ..... | 424/443 |

* cited by examiner

*Primary Examiner*—Alton N Pryor
(74) *Attorney, Agent, or Firm*—Fehr Law Firm; Thompson E. Fehr

(57) ABSTRACT

An antimicrobial composition comprising metal particles that may be silver, copper, or gold together with a surfactant such as benzalkonium chloride in a liquid medium, which is preferably deionized water, that will not react with the other constituents of the antimicrobial composition. Preferably, the composition also comprises a source of iodine, such as poly (vinyl pyrrolidone)-iodine complex. And a substrate carrier having the same type of metal as the particles deposited onto it may also be introduced into the liquid medium. The metal particles are preferably nanoparticles but may be in the micron size, in the submicron size, or bulk particles.

4 Claims, No Drawings

ANTIMICROBIAL COMPOSITION

BACKGROUND OF THE INVENTION

1. Field of the Invention

This invention relates to a composition for destroying microbes, which are defined herein as viruses, bacteria, fungi, and toxins.

2. Description of the Related Art

Metals such as silver, copper, and gold; surfactants such as benzalkonium chloride; and iodine, such as that from the poly(vinyl pyrrolidone)-iodine (PVP-I) complex are known to be effective antimicrobial agents. In fact, PVP-I is known to kill some types of avian flu, as explained in the journal *Dermatology* 2006; 212 Suppl. 1:115-8.

And substrate carriers for metal particles are also known in the art as a way for preventing the agglomeration of particles in a liquid medium.

BRIEF SUMMARY OF THE INVENTION

The present inventors have, however, surprisingly discovered that a composition comprising particles of a metal selected from the group consisting of silver, copper, and gold and a surfactant, preferably one having antimicrobial properties, has synergistic antimicrobial properties. (Only silver has actually been used in the manufactured composition.)

Preferably, the composition also includes a source of iodine.

The composition is prepared within a liquid medium with which constituents of the composition will not react, such as de-ionized water, distilled water, isopropyl alcohol, ethyl alcohol, tap water, and aqueous solutions of the alcohols. De-ionized water is preferred.

And, optionally, any substrate carrier for metal particles known in the art may also be included.

DETAILED DESCRIPTION OF THE INVENTION

As indicated above, the Antimicrobial Composition of the present invention comprises particles of a metal selected from the group consisting of silver, copper, and gold and a surfactant, preferably one having antimicrobial properties. Also the composition preferably comprises a source of iodine.

The particles of metal are preferably nanoparticles, which is defined herein as having a maximum dimension that is less than 100 nanometers since they can release more silver, but can be larger, including particles in the micron and submicron size range as well as bulk particles. Such larger particles are preferably large surface area porous particles.

The preferred surfactant is the quartenary ammonium salt benzalkonium chloride. It is, as mentioned above, preferred that the surfactant, itself, be antimicrobial; but any surfactant which helps to disperse silver particles in a liquid medium is sufficient. A nonexclusive list of acceptable surfactants includes poly(ethyleneimine) and DAXAD 19 distributed by GEO Specialty Chemicals of Deer Park, Tex.

And the preferred source of iodine is the poly(vinyl pyrrolidone)-iodine (PVP-I) complex, which deters agglomeration of the metal particles in a liquid medium. A nonexclusive list of other acceptable sources of iodine includes tincture of iodine and iodine salts.

When a source of iodine is not utilized, the amount of the surfactant is preferably increased.

And, optionally, any substrate carrier for metal particles that is known in the art may be added. Such substrate carriers include, but are not limited to, hydroxyapatite, carbon, boehmite, goethite, generic latex nano- to micron-size particles, polystyrene latex, silver-deposited aluminum oxide, zinc oxide, titanium dioxide, copper oxide, copper hydroxide, chromium oxide, and molybdenum oxide.

The Anticmicrobial Composition of the present invention is preferably made as follows:

A liquid medium with which constituents of the composition will not react, such as de-ionized water, distilled water, isopropyl alcohol, ethyl alcohol, tap water, and aqueous solutions of the alcohols is selected. De-ionized water is preferred.

A surfactant is added to the liquid medium. The acceptable range, by weight, is preferably 0.1 percent to 2.0 percent of the weight of the final product, with 0.1 percent being the most preferred when the source of iodine is the poly(vinyl pyrrolidone)-iodine (PVP-I) complex since an excess of PVP-I and benzalkonium chloride produces an undesired precipitate.

The particles of metal are then introduced into the surfactant liquid medium product.

A source of iodine is optionally added to the resultant suspension in a range that depends upon the source of iodine, but which is, by weight, for the PVP-I complex, 0.25 percent to 2.0 percent with 2.0 percent being preferred.

Rather than adding metal particles to the liquid medium, metal can be deposited to cover fully or partially a substrate carrier that is introduced into the liquid medium; or both the metal particles and metal-deposited substrate carrier can be introduced into the liquid medium.

And when a source of iodine is utilized, it is preferable to add such source prior to adding the substrate carrier for metal particles, if such substrate carrier is employed, since it is generally desirable to place into a liquid medium first those components which are readily soluble.

Example

Two solutions, designated OAT1 and OAT2 were created, mixed, and then tested against microbes.

OAT1 was generated as follows:

To 78 grams of a dilute suspension of (a) well-dispersed silver nanoparticles in deionized water, with the silver constituting approximately 0.1 percent or less, by weight, of the final product, and (b) 0.1 percent, by weight of the final product, of benzalkonium chloride, was added 20 grams of silver-deposited aluminum oxide (with the silver deposition being 4 to 8 percent, by weight, of the silver-deposited aluminum oxide). Lastly, 2.0 grams of poly(vinyl pyrrolidone)-iodine (PVP-I) complex was added.

OAT2 was made in the same manner except that the poly (vinyl pyrrolidone)-iodine (PVP-I) complex was added before the addition of the silver-deposited aluminum oxide.

The combined OAT1 and OAT2 were then tested against the avian influenza virus, Type A, (H9N2), Turkey/Wis/66; SPAFAS through injection into embryonated chicken eggs. A virus suspension control was used for comparison purposes The results were as follows:

| Exposure Time | Test Results (EID/ELD$_{50}$/mL) | Virus Suspension Control (EID/ELD$_{50}$/mL) | Log$_{10}$ Reduction |
|---|---|---|---|
| 1 minute | $\leq 10^{1.50}$ | $\geq 10^{7.50}$ | $\geq 6.00$ |
| 5 minutes | $\leq 10^{1.50}$ | $\geq 10^{7.50}$ | $\geq 6.00$ |

After application of the product to an item to be protected, such as, but not necessarily limited to, filter media or a textile, the solvent evaporates, leaving the Antimicrobial Composition of the present invention.

As used herein, the term "preferable" or "preferably" means that a specified element or technique is more acceptable than another but not that such specified element or technique is a necessity.

We claim:

1. An antimicrobial composition, which comprises:
   silver nanoparticles;
   benzalkonium chloride; and
   poly(vinyl pyrrolidone)-iodine complex.

2. An antimicrobial composition, which comprises:
   silver particles in the micron size;
   benzalkonium chloride; and
   poly(vinyl pyrrolidone)-iodine complex.

3. An antimicrobial composition, which comprises:
   silver particles in the submicron size;
   benzalkonium chloride; and
   poly(vinyl pyrrolidone)-iodine complex.

4. An antimicrobial composition, which comprises:
   bulk silver particles;
   benzalkonium chloride; and
   poly(vinyl pyrrolidone)-iodine complex.

* * * * *